United States Patent [19]

La Spina et al.

[11] 3,931,059
[45] Jan. 6, 1976

[54] PROCESS FOR PREPARING POLYCARBODIIMIDE FOAMS IN THE PRESENCE OF PHOSPHETANE OXIDE OR SULFIDE ADDUCTS

[75] Inventors: Andrea La Spina, Garbagnate Milanese, Italy; Werner Dietrich; Reinhard Schliebs, both of Cologne, Germany

[73] Assignee: Bayer Aktiengesellschaft, Leverkusen Bayerwerk, Germany

[22] Filed: Aug. 19, 1974

[21] Appl. No.: 498,788

[30] Foreign Application Priority Data
Aug. 21, 1973 Germany............................ 2342148

[52] U.S. Cl.... 260/2.5 BF; 260/2.5 AB; 260/429.9; 260/606.5 P; 260/DIG. 24
[51] Int. Cl.² ................... C08G 18/14; C08G 18/16
[58] Field of Search... 260/2.5 AB, 2.5 BF, 2.5 AW, 260/75 NB, 77.5 AB

[56] References Cited
UNITED STATES PATENTS

| | | | |
|---|---|---|---|
| 3,657,161 | 4/1972 | Bernard et al. | 260/2.5 AW |
| 3,717,596 | 2/1973 | Kan et al. | 260/2.5 AW |
| 3,723,364 | 3/1973 | McLaughlin et al. | 260/2.5 AW |
| 3,723,366 | 3/1973 | Kan | 260/2.5 AW |
| 3,728,289 | 4/1973 | Reuter et al. | 260/2.5 AB |
| 3,746,709 | 7/1973 | Patton et al. | 260/2.5 AW |
| 3,766,103 | 10/1973 | Patton et al. | 260/2.5 AW |

*Primary Examiner*—H. S. Cockeram
*Attorney, Agent, or Firm*—Joseph C. Gil

[57] ABSTRACT

A compound adapted to be used to advantage as a catalyst for making carbodiimide foams is prepared by a process wherein a. a phosphetane oxide or phosphetane sulphide of the general Formulae I and II:

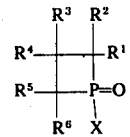 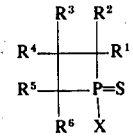

(I)        (II)

wherein

X represents a $C_1$–$C_{18}$ alkyl, $C_2$–$C_{18}$ alkenyl, $C_6$–$C_{14}$ aryl, $C_7$–$C_{20}$ aralkyl, $C_1$–$C_{18}$ alkoxy or $C_6$–$C_{14}$ aroxy group and $R^1$ to $R^6$ represent hydrogen and/or $C_1$–$C_4$ alkyl groups and is reacted with b. a mono-, di- and/or polyhydric alcohol having a molecular weight of about 32 to about 250, a protonic acid which has a pH of between 1 and 8 in N/10 aqueous solution, a metal salt or an acid chloride.

8 Claims, No Drawings

PROCESS FOR PREPARING POLYCARBODIIMIDE FOAMS IN THE PRESENCE OF PHOSPHETANE OXIDE OR SULFIDE ADDUCTS

This invention relates generally to polycarbodiimides and more particularly to compounds adapted to be used as catalysts in making polycarbodiimide foams.

It is known to produce polyurethane foams from organic polyols and organic polyisocyanates with the aid of catalysts such as tertiary amines and/or metal compounds. Blowing agents such as water and/or organic low boiling compounds, preferably halogenated alkanes such as monofluorotrichloromethane and the like are often used. These polyurethane foams generally have poor flame resistance so it is necessary to add flame retardants, e.g. compounds which contain phosphorus and/or halogen, in order to obtain incombustible or flame resistant foams.

Furthermore, it has been disclosed, e.g. in German Pat. No. 1,130,594, that foam plastics with carbodiimide groups which frequently have better flame reistance than polyurethane foams can be obtained from organic polyisocyanates in the presence of phospholines or their salts and oxides.

In Belgian Pat. No. 567,835, a similar process is described for producing foam plastics which contain carbodiimide groups from polyisocyanates in the presence of phospholine oxide as a catalyst.

These processes, however, still have numerous disadvantages which limit their industrial use, for example, carbodiimide-containing foams produced by them which have a substantially closed cell structure combined with extremely low densities have a strong tendency to shrink.

A further disadvantage which restricts the commercialization of the known processes lies in the fact that, if low catalyst concentrations are used, the foams take more than 1 to 2 hours to harden in a heated mold. Although tough foams can be obtained by a very rapid reaction even at room temperature if high concentrations of conventional catalysts are used (2 to 5%, based on the quantity of isocyanate), the reaction mixture containing these catalyst concentrations reacts so rapidly that it becomes difficult in practice to mix the polyisocyanate and catalyst homogeneously and discharge the mixture from the mixing apparatus before solidification; i.e. the starting time is too short.

It is also known that phosphetane oxides can be used as carbodiimidization catalysts.

Unchanged phosphetane oxides, however, are so highly reactive that they are unsuitable for the production of polycarbodiimide foams.

On the other hand, foams which have a polycarbodiimide structure have excellent flame resistance even at low densities so that they are of considerable commercial and economic interest and the solution of the problems mentioned above therefore constitutes an important technical advance.

One method of solving the technical problem mentioned above is disclosed in Belgium Patent 804,855 in the name of the present Applicants.

This earlier application relates to addition compounds of a. phosholine oxides, phosholine sulphides, phospholane oxides and phospholane sulphides and b. mono-, di- and/or polyalcohols with molecular weights of 32 to 250 or protonic acids which have pH values of 1 to 8 in N/10, aqueous solution or metal salts or acid chlorides and to the use of these catalysts for producing hard or rigid foams which contain carbodiimide groups.

It is an object of this invention to provide a novel and improved method for making polycarbodiimide foams. Another object of the invention is to provide a method for making polycarbodiimide foams which are tough and dimensionally stable. Still another object of the invention is to provide new polyaddition products which are catalysts for the reactions which produce a polycarbodiimide foam.

The foregoing objects and others are accomplished in accordance with this invention, generally speaking, by providing addition compounds prepared by reacting a. a phosphetane oxide or phosphetane sulphide of the general Formulae I and II:

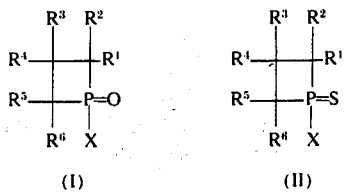

wherein

X represents a $C_1$–$C_{18}$ alkyl, $C_2$–$C_{18}$ alkenyl, $C_6$–$C_{14}$ aryl, $C_7$–$C_{20}$ aralkyl, $C_1$–$C_{18}$ alkoxy or $C_6$–$C_{14}$ aroxy group and $R^1$ to $R^6$ represent hydrogen and/or $C_1$–$C_4$ alkyl groups and b. a mono-, di- and/or polyhydric alcohol having a molecular weight of about 32 to about 250, a protonic acid which has a pH of between 1 and 8 in N/10 aqueous solution, a metal salt or an acid chloride.

Addition compounds prepared by reacting a. 1-oxo-1,2,2,3,4,4-hexamethyl-phosphetane and b. glycerol, ethylene glycol, oxalic acid, phosphorus oxychloride, hydrochloric acid or zinc chloride are particularly preferred catalysts for making polycarbodiimide foams.

The invention thus provides new catalysts with which tough and dimensionally stable, i.e. non-shrinking foams with a polycarbodiimide structure can be prepared in a relative short reaction time at room temperature.

Any suitable compound prepared from (a) and (b) above may be used to advantage as a catalyst in the production of polycarbodiimide foams such as, for example, a. 1-Oxo-1,2,2,3,4,4-hexamethylphosphetane and
b. aluminum chloride;

a. 1-Oxo-1,2,2,3,4,4-hexamethylphosphetane and
b. formic acid;

1-Oxo-1,2,2,3,4,4-hexamethylphosphetane and
b. sulphuric acid;

a. 1-Oxo-1,2,2,3,4,4-hexamethylphosphetane and
b. zinc chloride;

a. 1-Oxo-1,2,2,3,4,4-hexamethylphosphetane and
b. zinc acetate;

a. 1-Oxo-1,2,2,3,4,4-hexamethylphosphetane and
b. antimony trichloride;

a. 1-Oxo-1,2,2,3,4,4-hexamethylphosphetane and
b. phosphorus oxychloride;

a. 1-Oxo-1,2,2,3,4,4-hexamethylphosphetane and
b. methane phosphonic acid dichloride;

a. 1-Thio-1-phenyl-2,2,3,4,4-pentamethylphosphetane and
b. glycerol;
a. 1-Thio-1-phenyl-2,2,3,4,4-pentamethylphosphetane and
b. ethylene glycol; and the like.

The phosphetanes used for preparing the addition compounds according to the invention are known per se.

The phosphetane oxides and phosphetane sulphides used may be any phosphorus compound of the following Formulae I and II:

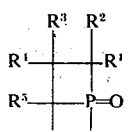  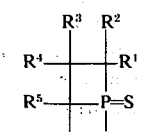

(I)  (II)

wherein

X represents a $C_1$–$C_{18}$ alkyl, $C_2$–$C_{18}$ alkenyl, $C_6$–$C_{14}$ aryl, $C_7$–$C_{20}$ aralkyl, $C_1$–$C_{18}$ alkoxy or $C_6$–$C_{14}$ aroxy group and $R^1$ to $R^6$ denote hydrogen and/or $C_1$–$C_4$ alkyl groups.

Examples of suitable phosphorous compounds include:
1-oxo-1,2,2,3,4,4-hexamethylphosphetane,
1-oxo-1-benzyl-2,2,3,4,4-pentamethyl-phosphetane,
1-oxo-1-methoxy-2,2,3,4,4-pentamethyl-phosphetane,
1-oxo-1-t-butyl-2,2,3,4,4-pentamethyl-phosphetane,
1-thio-1-phenyl-2,2,3,4,4-pentamethyl-phosphetane,
1-oxo-1-phenyl-2,2,3,3,4-pentamethyl-phosphetane,
1-thio-1-phenyl-2,2,3,3-tetramethyl-phosphetane,
1-oxo-1-phenyl-2,2,3,3-tetramethyl-phosphetane,
1-oxo-1-methoxy-2,2,3-trimethyl-phosphetane,
1-oxo-1-phenyl-2,2,3-trimethyl-phosphetane,
1-oxo-1-phenyl-2,2,4,4-tetramethyl-3-i-propyl-phosphetane,
1-oxo-1-methoxy-2,3,4,4-tetramethyl-phosphetane
and the like.

Any suitable mono-, di- and/or polyalcohol having a molecular weight of from about 32 to about 250 (component b) may be used for preparing the addition compounds according to the invention such as, for example, methanol, ethanol, butanol, isopropanol, ethylene glycol, di- and triethylene glycol, propane-1,3- and -1,2-diol, butane-1,3- and -1,4-diol, glycerol, trimethylolpropane, hexane-1,6-diol, hexane-1,2,6-triol and the like. Preferred polyalcohols are alcohols with valencies of 3 to 8. Most preferred alcohols are mono-alcohols, diols and triols.

Any suitable protonic acid which as a pH of between 1 and 8 in N/10 aqueous solution may be used as component b. Preferred protonic acids are mono-, di- and/or polycarboxylic acids having a molecular weight of about 46 to about 250 and mineral acids known per se. The following are examples of suitable protonic acids: formic acid, acetic acid, propionic acid, butyric acid, mono-, di- and trichloro-acetic acid, oxalic acid, fumaric acid, maleic acid, adipic acid and the like. Suitable mineral acids are e.g. hydrochloric, hydrobromic and hydriodic acid, o-phosphoric acid, boric acid, sulphuric acid, phosphorous acid and the like.

Any suitable metal salt may be used as component b such as, for example, zinc chloride, tin(II) bromide, tin(IV) chloride, magnesium chloride, calcium chloride, lithium chloride, lithium iodide, cadmium chloride, manganese(II) chloride, vanadium oxytrichloride and the like. The acid chlorides used (also component b) may be inorganic or hetero organic and may contain e.g. the elements sulphur, phosphorus, silicon, arsenic and antimony. The following are examples of suitable acid chlorides: phosphorus(III) chloride, phosphorus oxy-tribromide, phosphorus oxychloride, antimony(V) chloride, silicon(IV) chloride, methyl trichlorosilane, methane phosphonic acid dichloride, methane sulphonic acid chloride, p-toluene sulphonic acid chloride and 1-chloro-1-oxophospholine and the like.

To prepare the addition compounds according to the invention, component (a) and component (b) are mixed together in a molar ratio of between 1 : 20 and 20 : 1, preferably between 1 : 5 and 5 : 1 and more particularly between 3 : 1 and 1 : 2. Inert solvents such as benzene, ethyl acetate or acetone and particularly chloroform may be used. The new addition compounds may be partially isolated by crystallization.

The addition compounds according to the invention are in many cases oily substances or crystalline compounds which can be identified e.g. by means of their infra red and/or nuclear magnetic resonance spectra or by their formation enthalpy.

Distinct shifts in the nuclear magnetic resonance spectrum are obtained when 1-methyl-1-oxophosphetanes are used. The shift in the band position is given in the examples wherever it is used to identify the compounds obtained.

This invention also provides a process for the production of addition compounds which contain phosphorus, characterized in that a a. Phosphetane oxide or phosphetane sulphide of the general formulae I and II

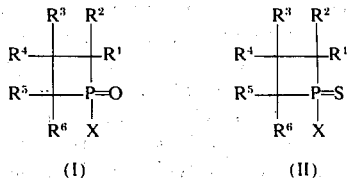

wherein

X represents a $C_1$–$C_{18}$ alkyl, $C_2$–$C_{18}$ alkenyl, $C_6$–$C_{14}$ aryl, $C_7$–$C_{20}$ aralkyl, $C_1$–$C_{18}$ alkoxy or $C_6$–$C_{14}$ aroxy group and $R^1$ to $R^6$ represent hydrogen and/or $C_1$–$C_4$ alkyl groups is mixed with b. a mono-, di- and/or polyhydric alcohol having a molecular weight of about 32 to about 250 or a protonic acid which has a pH of between 1 and 8 in N/10 aqueous solution or a metal salt or acid chloride in a molar ratio of 1 : 20 to 20 : 1, preferably 5 : 1 to 1 : 5 and particularly 3 : 1 to 1 : 2, optionally in the presence of inert solvents.

By using the addition compounds provided by the invention as catalysts for the production of foam plastics which contain carbodiimide groups, a starting time sufficiently long for vigorous mixing and discharge of the mixture from the mixing apparatus is obtained even at high catalyst concentrations and, once the reaction has begun, conversion of the organic polyisocyanate to a foam resin which contains carbodiimide groups can be completed within a short time, even at room temperature. A particularly advantageous course of the reaction, i.e. a long starting time followed by a rapid foaming process, is obtained with those addition compounds in which component (b) is capable of reacting with isocyanates.

The polycarbodiimide foams which can be produced from polyisocyanates with the aid of the addition compounds according to the invention generally have densities of from 5 to 100 kg/m³, preferably 10 to 30 kg/m³, and have stable contours and are distinguished by their excellent dimensional stability under heat and excellent flame resistance. By flame resistance is meant that the foams are "self-extinguishing" according to ASTM D 1692 or "flame-resistant" according to DIN 4102.

A further object of this invention is therefore a process for the production of hard or rigid foam plastics which contain carbodiimide groups from organic polyisocyanates in the presence of catalysts which form carbodiimide groups, water and/or organic blowing agents, characterized in that the catalysts used are addition compounds of a. phosphetane oxide or phosphetane sulphide of the general formulae I and II:

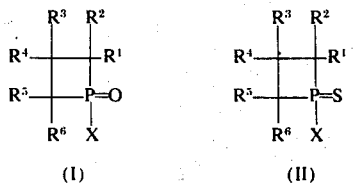

wherein

X represents a $C_1-C_{18}$ alkyl, $C_2-C_{18}$ alkenyl, $C_6-C_{14}$ aryl, $C_7-C_{20}$ aralkyl, $C_1-C_{18}$ alkoxy or $C_6-C_{14}$ aroxy group and $R^1$ to $R^6$ represent hydrogen and/or $C_1-C_4$ alkyl groups, and b. a mono-, di- and/or polyalcohol with a molecular weight of about 32 to about 250, a protonic acid which has a pH of between 1 and 8 in N/10 aqueous solution, a metal salt or an acid chloride, in any catalytic amount such as, for example, 0.5% to 20 percent by weight, preferably 1 to 10 percent by weight, based on the quantity of polyisocyanate.

According to a special variation of the process of the invention, a mixture which is stable when stored at room temperature is prepared from an organic polyisocyanate, a catalyst and optionally conventional foaming agents such as emulsifiers and/or stabilizers. The foaming process can then be started by simply heating this mixture to temperatures of between 40° and 200°C, preferably 50° to 150°C.

The following addition compounds are examples of preferred catalysts for this variation of the process: 1-Oxo-1,2,2,3,4,4-hexamethylphosphetane and hydrogen chloride; 1-oxo-1,2,2,3,4,4-hexamethylphosphetane and phosphorus oxychloride; 1-oxo-1,2,2,3,4,4-hexamethylphosphetane and zinc chloride; 1-oxo-1-phenyl-2,2,3,3,4-pentamethyl-phosphetane and calcium chloride.

Any suitable organic polyisocyanate may be used for the process according to the invention such as, for example, aliphatic, cycloaliphatic, araliphatic, aromatic or heterocyclic polyisocyanates such as those described e.g. by W. Siefken in Justus Liebigs Annalen der Chemie, 562, pages 75 to 136, for example, ethylene diisocyanate, tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and any mixtures of these isomers; 1-isocyanato-3,3,5-trimethyl-5-isocyanatomethyl-cyclohexane (German Auslegeschrift No. 1,202,785); hexahydrotolylene-2,4- and -2,6-diisocyanate and any mixtures of these isomers; hexahydrophenylene-1,3-and/or -1,4-diisocyanate; perhydrodiphenylmethane-2,4'-and/or -4,4'-diisocyanate; phenylene-1,3- and -1,4-diisocyanate; tolylene-2,4- and -2,6-diisocyanate and any mixtures of these isomers; diphenylmethane-2,4'- and/or 4,4'-diisocyanate; naphthylene-1,5-diisocyanate; triphenylmethane-4,4',4''-triisocyanate; polyphenyl-polymethylene-polyisocyanates which can be obtained by aniline-formaldehyde condensation followed by phosgenation and which have been described e.g. in British Pat. Specifications No. 874,430 and 848,671; perchlorinated aryl polyisocyanates as described e.g. in German Auslegeschrift No. 1,157,601; polyisocyanates which contain carbodiimide groups as described in German Pat. No. 1,092,007; the diisocyanates described in U.S. Pat. No. 3,492,330; polyisocyanates which contain allophanate groups as described e.g. in British Pat. Specification No. 994,890; Belgian Pat. No. 761,626 and published Dutch Pat. application No. 7,102,524; polyisocyanates which contain isocyanurate groups as described e.g. in German Pat. No. 1,022,789; 1,222,067 and 1,027,394 and in German Offenlegungsschriften No. 1,929,034 and 2,004,048; polyisocyanates which contain urethane groups as described e.g. in Belgian Pat. No. 752,261 or in U.S. Pat. No. 3,394,164; polyisocyanates which contain acylated urea groups in accordance with German Pat. No. 1,230,778; polyisocyanates which contain biuret groups as described e.g. in German Pat. No. 1,101,394; in British Pat. Specification No. 889,050 and in French Pat. No. 7,017,514; polyisocyanates which are prepared by telomerization reactions as described e.g. in Belgian Pat. No. 723,640; polyisocyanates which contain ester groups as described e.g. in British Pat. Specifications No. 956,474 and 1,072,956; in U.S. Pat. No. 3,567,763 and in German Pat. No. 1,231,688; and reaction products of the above mentioned isocyanates with acetals according to German Pat. No. 1,072,385.

Aromatic isocyanates are preferred for the purpose of the invention.

The distillation residues obtained from the commercial production of isocyanates such as polymers of 4,4'-diphenylmethane diisocyanate which still contain isocyanate groups may also be used, and may be dissolved in one or more of the above mentioned polyisocyanates. Any mixtures of the above mentioned polyisocyanates may also be used.

It is generally particularly preferred to use commercially readily obtainable organic polyisocyanates such as tolylene-2,4- and -2,6-diisocyanate and any mixtures of these isomers (TDI); polyphenyl-polymethylene-polyisocyanates which can be obtained by aniline-formaldehyde condensation followed by phosgenation (crude MDI) and polyisocyanates which contain carbodiimide, urethane, allophanate, isocyanurate, urea or biuret groups (modified polyisocyanates).

It is also particularly advantageous to use, as polyisocyanates, the undistilled phosgenation products of tolylenediamine or mixtures of 2,4- and/or -2,6-tolylene diisocyanate and 5-60% by weight, preferably 10-50% by weight of the distillation residue obtained from the production of tolylene diisocyanate as well as mixtures of polyisocyanates which are obtained by the condensation of aniline with formaldehyde followed by phosgenation and 5% to 50% by weight, preferably 10% to 30% by weight, of the distillation residue obtained from the production of tolylene diisocyanate. The reason why these products are preferred is that it has been found that the catalysts according to the invention are not attacked by the azide compounds and, particularly, chlorine compounds present in crude isocyanate mixtures, e.g. in crude tolylene diisocyanate or crude diisocyanatodiphenyl methane.

According to the invention, it is often preferred to include up to 50 equivalents percent, based on the quantity of isocyanate, of compounds with a molecular weight of about 62 to about 10,000 which contain at least two hydrogen atoms which are reactive with isocyanates, e.g. ethylene glycol, propylene-1,3-glycol, hexane-1,6-diol, tripropylene glycol or polypropylene glycol with a molecular weight of about 400.

Among the compounds which contain at least two hydrogen atoms which are reactive with isocyanates, those with a molecular weight of from about 400 to about 10,000 are generally preferred. In addition to compounds which contain amino, thiol or carboxyl groups, the compounds of this kind are preferably polyhydroxyl compounds, in particular those which contain 2 to 8 hydroxyl groups and especially those with a molecular weight of about 800 to about 10,000, preferably 1000 to 6000, e.g. polyesters, polyethers, polythioethers, polyacetals, polycarbonates and polyester amides which contain at least 2 and generally 2 to 8 but preferably 2 to 4 hydroxyl groups; these compounds are known per se for the production of homogeneous and cellular polyurethanes.

Any suitable hydroxyl polyester may be used, for example, products obtained by reacting polyhydric alcohols, preferably dihydric alcohols to which trihydric alcohols may be added, with polybasic, preferably dibasic carboxylic acids. Instead of free polycarboxylic acids, the corresponding polycarboxylic acid anhydrides or corresponding polycarboxylic acid esters of lower alcohols or mixtures thereof may be used for preparing the polyesters. The polycarboxylic acids may be aliphatic, cycloaliphatic, aromatic and/or heterocyclic and may be substituted, e.g. with halogen atoms and/or unsaturated. The following are examples: succinic acid, adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride, tetrachlorophthalic acid anhydride, endomethylene tetrahydrophthalic acid anhydride; glutaric acid anhydride; maleic acid; maleic acid anhydride; fumaric acid; dimeric and trimeric fatty acid such as oleic acid which may be mixed with monomeric fatty acids, dimethyl terephthalate and bis-glycol terephthalate. The following are examples of suitable polyhydric alcohols: ethylene glycol; propylene-1,2- and -1,3-glycol; butylene-1,4- and -2,3-glycol; hexane-1,6-diol; octane-1,8-diol, neopentyl glycol; cyclohexane dimethanol (1,4-bis-hydroxymethylcyclohexane); 2-methyl-propane-1,3-diol; glycerol; trimethylolpropane; hexane-1,2,6-triol, butane-1,2,4-triol; trimethylolethane; pentaerythritol; quinitol; mannitol and sorbitol; methyl glycoside, diethylene glycol; trimethylene glycol; tetraethylene glycol; polyethylene glycols, dipropylene glycol; polypropylene glycols; dibutylene glycol and polybutylene glycols. The polyesters may contain a proportion of carboxyl end groups. Polyesters of lactones such as ε-caprolactone or hydroxycarboxylic acids such as ω-hydroxycaproic acid may also be used.

Any suitable polyether which contains at least two and generally 2 to 8, preferably 2 or 3 hydroxyl groups may be used. Such polyethers are known per se and are prepared e.g. by polymerizing epoxides such as ethylene oxide, propylene oxide, butylene oxide, tetrahydrofuran, styrene oxide or epichlorohydrin with themselves, e.g. in the presence of boron trifluoride, or by a process of addition of these epoxides, either as mixtures or successively, to starting components which contain reactive hydrogen atoms such as alcohols or amines, e.g. water, ethylene glycol, propylene-1,3- or -1,2-glycol, trimethylolpropane, 4,4'-dihydroxydiphenylpropane, aniline, ammonia, ethanolamine or ethylene diamine. Sucrose polyethers e.g. those described in German Auslegeschriften No. 1,176,358 and 1,064,938, may also be used according to the invention. It is frequently preferred to use those polyethers which contain predominantly primary hydroxyl groups (up to 90% by weight, based on all the hydroxyl groups present in the polyether). Polyethers which have been modified with vinyl polymers, e.g. the products obtained by polymerizing styrene or acrylonitrile in the presence of polyethers (U.S. Pat. No. 3,383,351; 3,304,273; 3,523,093 and 3,110,695 and German Pat. No. 1,152,536) and polybutadienes which contain hydroxyl groups are also suitable.

Any suitable polythioether may be used such as, for example, the condensation products of thiodiglycol with itself and/or with other glycols, dicarboxylic acids, formaldehyde, aminocarboxylic acids or aminoalcohols. The products obtained are either polythio mixed ethers, polythioether esters or polythioether ester amides, depending on the co-component.

The polyacetals used may be, for example, the compounds which can be prepared from glycols such as diethylene glycol, triethylene glycol, 4,4'-dioxethoxy-diphenyldimethyl-methane, hexanediol and formaldehyde. Polyacetals suitable for the purpose of the invention may also be prepared by polymerizing cyclic acetals.

Any suitable polycarbonate with hydroxyl groups may be used such as the kind known per se which can be prepared, for example, by reacting diols such as propane-1,3-diol, butane-1,4-diol and/or hexane-1,6-diol, diethylene glycol, triethylene glycol or tetraethylene glycol with diarylcarbonates, e.g. diphenyl carbonate or phosgene.

Suitable polyester amides and polyamides include e.g. the predominantly linear condensates obtained from polyvalent saturated and unsaturated carboxylic acids or their anhydrides and polyvalent saturated and unsaturated amino alcohols, diamines, polyamines and their mixtures.

Polyhydroxyl compounds which already contain urethane or urea groups as well as natural polyols which may be modified such as castor oil, carbohydrates or starch may also be used. Addition products obtained by reacting alkylene oxides with phenol formaldehyde resins or with urea formaldehyde resins may also be used according to the invention.

Representatives of these compounds which may be used according to the invention have been described e.g. in High Polymers, Vol. XVI, "Polyurethanes, Chemistry and Technology" by Saunders-Frisch, Interscience Publishers, New York, London, Volume I, 1962, pages 32 – 42 and pages 44 – 54 and Volume II, 1964, pages 5 – 6 and 198 – 199 and in Knuststoff-Handbuch, Volume VII, Vieweg-Höchtlen, publishers Carl-Hanser Verlag, Munich, 1966, e.g. on pages 45 to 71.

Water and/or any suitable readily volatile organic substance may be used as a blowing agent in addition to the carbon dioxide liberated by the formation of polycarbodiimide. Suitable organic blowing agents are e.g. acetone, ethyl acetate, methanol, ethanol, halogenated alkanes such as methylene chloride, chloroform, ethylidene chloride, vinylidene chloride, monofluorotrichloromethane, chlorodifluoromethane or dichlorodifluoromethane, butane, hexane, heptane, or diethyl ether. Compounds which decompose at temperatures above room temperature to liberate gases such as nitrogen, e.g. azo compounds such as azo isobutyric acid nitrile, may also act as blowing agents. Other examples of blowing agents and details of the methods of using them may be found in Kunststoff-Handbuch, Volume VII, published by Vieweg and Höchtlen, Carl-Hanser Verlag, Munich 1966, e.g. on pages 108 and 109, 453 to 455 and 507 to 510.

According to the invention, the catalysts commonly used in isocyanate chemistry may be used in addition to the addition compounds according to the invention. The following are examples of conventional catalysts which may be used along with the catalysts according to the invention: tertiary amines such as triethylamine; tributylamine; N-methyl-morpholine; N-ethyl-morpholine; N-cocomorpholine; N,N,N',N'-tetramethyl-ethylene diamine; 1,4-diazo-bicyclo-(2,2,2)-octane; N-methyl-N'-dimethyl-aminoethyl-piperazine; N,N-dimethylbenzylamine; bis-(N,N-diethylaminoethyl)-adipate; N,N-diethylbenzylamine, pentamethyl-diethylene triamine; N,N-dimethylcyclohexylamine; N,N,N',N'-tetramethyl-1,3-butanediamine; N,N-dimethyl-$\beta$-phenylethylamine; 1,2-dimethylimidazole and 2-methylimidazole.

The following are examples of suitable tertiary amine catalysts which contain hydrogen atoms that react with isocyanate groups: triethanolamine; triisopropanolamine; N-methyl-diethanolamine; N-ethyl-diethanolamine; N,N-dimethyl-ethanolamine and their reaction products with alkylene oxides such as propylene oxide and/or ethylene oxide.

Silaamines which contain carbon-silicon bonds may also be used as catalysts, e.g. the compounds described in German Pat. No. 1,229,290 such as 2,2,4-trimethyl-2-silamorpholine or 1,3-diethylaminomethyltetramethyl-disiloxane.

Bases which contain nitrogen, such as, tetraalkylammonium hydroxides, alkali metal hydroxides such as, sodium hydroxide, alkali metal phenolates such as sodium phenolate and alkali metal alcoholates such as sodium methylate may also be used as catalysts. Hexahydrotriazines are also suitable catalysts.

According to the invention, organic metal compounds may also be used as catalysts, especially organic tin compounds.

The organic tin compounds preferably used are the tin(II) salts of carboxylic acids such as tin(II) acetate, tin(II) octoate, tin(II) ethylhexoate and tin(II) laurate and the dialkyl tin salts of carboxylic acids such as dibutyl tin diacetate, dibutyl tin dilaurate, dibutyl tin maleate or dioctyl tin diacetate.

Other examples of catalysts to be used according to the invention and details of their mode of action may be found in Kunstsoff-Handbuch, Volume VII, published by Vieweg and Höchtlen, Carl-Hanser-Verlag, Munich 1966, e.g. on pages 96 to 102.

Any catalytic amount of the usual catalysts of isocyanate chemistry may be used such as, for example, between about 0.001% and 10% by weight, based on the quantity of compounds with a molecular weight of 400 to 10,000 which contain at least two hydrogen atoms that are reactive with isocyanates.

Surface active additives (emulsifiers and foam stabilizers) may also be used according to the invention. The emulsifiers used may be e.g. the sodium salts of ricinoleic sulphonates or of fatty acids or salts of fatty acids with amines such as oleic acid diethylamine or stearic acid diethanolamine. Alkali metal or ammonium salts of sulphonic acids such as the alkali or ammonium salts of dodecyl benzene sulphonic acid or of dinaphthylmethane disulphonic acid or of fatty acids such as ricinoleic acid or of polymeric fatty acids may also be used as surface active additives.

The foam stabilizers used are mainly water-soluble polyether siloxanes. These compounds are generally constructed so that a copolymer of ethylene oxide and propylene oxide is attached to a polydimethylsiloxane group. Foam stabilizers of this kind have been described, for example, in U.S. Pat. No. 3,629,308 the disclosure of which is incorporated herein by reference.

Reaction retarders, e.g. substances which are acid in reaction such as hydrochloric acid or organic acid halides, cell regulators known per se such as paraffins or fatty alcohols or dimethylpolysiloxanes, pigments, dyes and flame retarders known per se, e.g. tris-chloroethyl-phosphate or ammonium phosphate and polyphosphate, stabilizers against ageing and weathering, plasticizers, fungistatic and bacteriostatic substances and fillers such as barium sulphate, kieselguhr, carbon black or whiting may also be used according to the invention.

Other examples of surface active additives, foam stabilizers, cell regulators, reaction retarders, stabilizers, flame retarding substances, plasticizers, dyes and fillers and fungistatic and bacteriostatic substances which may also be used according to the invention and details concerning their methods of use and mode of action may be found in Kunststoff-Handbuch, Volume VI, published by Vieweg and Höchtlen, Carl-Hanser-Verlag, Munich 1966, e.g. on pages 103 to 113.

In certain cases, e.g. when foaming undistilled phosgenation products of tolylene diamine, it may be advantageous to use 0.5% to 20% by weight, preferably 1% to 10% by weight, based on the quantity of isocyanate, of isocyanurate-forming catalysts know per se in addition to the addition compounds according to the invention.

The catalysts used for the formation of isocyanurate groups are preferably those which cause gelling of the isocyanate with isocyanurate formation at a temperature of 20°C within 10 minutes when added in a quantity of 1 to 10 g per 100 g of organic polyisocyanate, e.g. sodium phenolate, potassium acetate, sodium trichlorophenolate, 2,4,6-tri-(dimethyl-aminomethyl) phenol or a mixture of 80% of ortho- and 20% of paradimethylaminomethylphenol.

The foam plastics which can be produced according to the invention have excellent flame resistance which can be even further improved by using known flame retarding agents such as compounds of halogens, of nitrogen, of phosphorus and of antimony.

Foaming may be carried out either by hand or mechanically by known techniques. Mechanical devices in which a mixture of activator and addition compound, foaming agent, to which polyols, blowing agents and flame-retarding agents, etc. may be added and the isocyanate component are delivered through separate pumps are advantageously used.

The foams according to the invention may be produced e.g. in the form of blocks, panels or endless webs, either intermittently or continuously, if desired also on double conveyor belts. Foams which have been produced by foaming without restriction of volume generally have a density of 5 to 25 kg/m³ while foams which have been produced by foaming in a closed mold may have a density of 25 to 100 kg/m³.

The foams containing carbodiimide groups are suitable for various types of insulation against cold and heat. Because of their excellent flame resistance, they are particularly suitable for use as insulation in walls of buildings and because of their high thermal resistance they are also suitable for the insulation of technical plants, particularly heating installations.

EXAMPLE 1

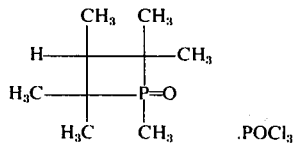

6.8 g of 1-oxo-1,2,2,3,4,4-hexamethyl-phosphetane and 150 ml of chloroform are introduced into a three-necked flask with stirrer and dropping funnel. 4 ml of phosphorus oxychloride are then added dropwise with constant stirring.

The reaction is exothermic. After termination of the reaction the chloroform is evaporated off. 12.8 g of a pale pink solid substance which melts at 189°C are obtained.

The band position of the methyl group on phosphorus is shifted by 2.95 ppm compared with the phosphetane used as starting material (solvent CD Cl₃).

EXAMPLE 2

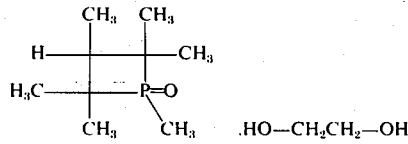

8.7 g of 1-oxo-1,2,2,3,4,4-hexamethylphosphetane, 3.1 g of ethylene glycol and 150 ml of chloroform are introduced into a flask with stirrer. The reaction mixture is heated to 20° to 30°C with stirring. The reaction is exothermic. After termination of the reaction, the chloroform is evaporated off under vacuum and 10 g of a pale yellowish oil are obtained. The band position of the methyl protons on phosphorus has shifted to 1.63 ppm (solvent CD Cl₃).

EXAMPLE 3

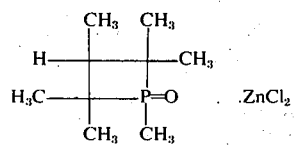

8.7 g of 1-oxo-1,2,2,3,4,4-hexamethyl-phosphetane, 6.8 g of zinc chloride and 150 ml of chloroform are reacted together as in Example 2. After removal of the chloroform by evaporation, 16 g of a violet colored addition compound are obtained. The methyl proton signal of the group attached to phosphorus has shifted to 1.84 ppm in this compound.

EXAMPLE 4

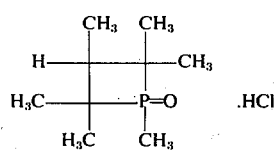

8.7 g of 1-oxo-1,2,2,3,4,4-hexamethyl-phosphetane, 30 ml of 37% aqueous hydrogen chloride and 150 ml of chloroform are reacted together as in Example 2. Water and chloroform are then evaporated off under vacuum. An oily addition compound is obtained. The band position of the methyl protons on the group attached to phosphorus is shifted to 1.8 ppm.

EXAMPLE 5

30 g of the addition compound described in Example 2 are heated to 50°C in a three-necked flask equipped with reflux condenser, thermometer and stirrer. 50 g of glycerol are then added dropwise in portions (2 to 3 g/min) with constant stirring. The reaction mixture is then heated to 100°C for 2 hours. An oily product is obtained after cooling to room temperature.

A mixture of 8 g of the adduct described above and 0.5 g of a polysiloxane-polyalkylene glycol (as foam stabilizer) is prepared in a paper cup. 100 g of polymeric diphenylmethane diisocyanate (obtained by condensation of aniline with formaldehyde followed by phosgenation) which has a viscosity of 200 cP/35°C and an isocyanate content of 31.2% are added to this mixture with vigorous stirring.

| Reaction times: | ⁺R = 120 sec | ⁺R = stirring time |
|---|---|---|
| | ⁺I = 170 sec | ⁺I = lying time |
| | ⁺A = 610 sec | ⁺A = setting time |
| | ⁺S = 730 sec | ⁺S 32 rising time |
| | ⁺K = 780 sec | ⁺K = tack-free time |

The foam obtained has the following physical properties

| Density: | 19 kg/m³ DIN 53420 |
|---|---|
| Compression strength: | 1.1 kg/cm² DIN 53421 |
| Resistance to bending under heat: | 125°C DIN 53424 |
| Coefficient of thermal conductivity: | 0.029 kcal/m/h/degree DIN 52612 |
| Small sample burning test: | 77-85 Fl. Kl DIN 4102 |

Pure 1-oxo-1,2,2,3,4,4-hexamethylphosphetane causes such a rapid reaction that homogeneous mixing of polyisocyanate with catalyst and discharge of the mixture involves great difficulties.

Any of the other addition compounds indicated as suitable as catalysts may be substituted for the one used in Example 5 and other organic polyisocyanates can be used instead of the poly (diphenylmethane diisocyanate) if desired.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. In a process for making a rigid foam plastic which contains carbodiimide groups from an organic polyisocyanate, the improvement which comprises includig a catalytic amount of an addition compound of
   a. a phosphetane oxide or phosphetane sulphide of the general formulae I and II

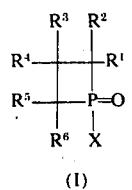
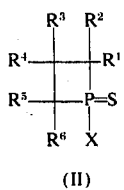

wherein
   X denotes a $C_1-C_{18}$ alkyl, $C_2-C_{18}$ alkenyl, $C_6-C_{14}$ aryl, $C_7-C_{20}$ aralkyl, $C_1-C_{18}$ alkoxy or $C_6-C_{14}$ aroxy group and
   $R^1$ to $R^6$ denote hydrogen and/or $C_1-C_4$ alkyl groups and
   b. a mono-, di- and/or polyhydric alcohol with a molecular weight of about 32 to about 250, a protonic acid which has a pH of between 1 and 8 in N/10 aqueous solution, a metal salt or an acid chloride and allowing the polyisocyanate to react.

2. The process of claim 1 wherein up to 50 equivalents percent, based on the quantity of isocyanate, of a compound with a molecular weight of about 62 to about 10,000, which contains at least two hydrogen atoms which are reactive with isocyanates are included in the reaction mixture.

3. The process of claim 1 wherein from about 0.5 to 20% by weight, based on the quantity of isocyanate, of a catalyst which forms isocyanurate groups is included in the reaction mixture.

4. The process of claimm 1 wherein the polyisocyanate is an undistilled phosgenation product of tolylene diamine or a mixture of tolylene-2,4- and/or -2,6-diisocyanate and 5% to 60% by weight of the distillation residue obtained from the production of tolylene diisocyanate.

5. The process of claim 1 wherein the polyisocyanate is a mixture of polyisocyanates obtained by the condensation of aniline with formaldehyde followed by phosgenation and 5% to 50% by weight, of the distillation residue obtained from the production of tolylene diisocyanate.

6. The process of claim 1 wherein a mixture which is stable when stored at room temperature containing the polyisocyanate and the catalyst is heated to 40° to 200°C to start foaming.

7. A process of making a polycarbodiimide foam from an organic polyisocyanate which comprises heating the polyisocyanate in the presence of a catalytic amount of an addition compound of a phosphetane or phosphetane sulphide and an alcohol, a protonic acid adapted to form a N/10 aqueous solution having a pH of 1 to 8, a metal salt or an acid chloride.

8. The process of claim 7 wherein a blowing agent, an organic polyisocyanate and a compound having at least two hydrogen atoms determined by the Zerewitinoff method are heated to form a polycarbodiimide-polyurethane or polyurea foam.

* * * * *